United States Patent
Alt et al.

[11] Patent Number: 6,073,049
[45] Date of Patent: *Jun. 6, 2000

[54] PROGRAMMABLY UPGRADABLE IMPLANTABLE CARDIAC PACEMAKER

[75] Inventors: Eckhard Alt, Ottobrunn, Germany; Lawrence J. Stotts, Lake Jackson, Tex.

[73] Assignee: Sulzer Intermedics, Inc., Angleton, Tex.

[*] Notice: This patent is subject to a terminal disclaimer.

[21] Appl. No.: 08/960,560

[22] Filed: Oct. 29, 1997

Related U.S. Application Data

[63] Continuation-in-part of application No. 08/648,707, May 16, 1996, Pat. No. 5,725,559.

[51] Int. Cl.$^7$ ............................................. A61N 1/36
[52] U.S. Cl. ................................. 607/31; 607/59; 607/9; 128/903
[58] Field of Search ............................. 607/4, 5, 30–32, 607/9, 59, 60; 128/903

[56] References Cited

U.S. PATENT DOCUMENTS

| | | |
|---|---|---|
| 4,388,929 | 6/1983 | Renirie et al. . |
| 4,590,944 | 5/1986 | Mann et al. . |

FOREIGN PATENT DOCUMENTS

| | | |
|---|---|---|
| 0 730 882 | 9/1996 | European Pat. Off. . |
| 2 079 610 | 1/1982 | United Kingdom . |
| WO 93/08872 | 5/1993 | WIPO . |
| WO 93/09841 | 5/1993 | WIPO . |

*Primary Examiner*—Jeffrey R. Jastrzab
*Attorney, Agent, or Firm*—Blank Rome Comisky & McCauley LLP

[57] ABSTRACT

An implantable cardiac pacemaker is adapted to be selectively non-invasively upgraded from time to time after implantation to provide a plurality of different diagnostic, functional, and pacing operational modes in the form of respective combinations of single and dual chamber sensing and pacing and rate-adaptive pacing of a patient's heart to correct any of various cardiac arrhythmias attributable to cardiac pacing or cardiovascular disorders, and of extended memory and physiological monitoring functions. The pacemaker is implemented to make available the plurality of different pacing operational and other functional modes, and is programmable to selectively enable current operation of at least one of the available pacing operational modes according to current needs of the patient while inhibiting current operation of all other available pacing operational modes and any other non-selected functional modes. Subsequently, the implanted pacemaker may be programmed non-invasively to selectively restore operation of at least one of the inhibited pacing operational modes or other functional modes when the patient evidences a need therefor, but the selective restoration programming is locked out unless performed with a prescribed security access key. Additional charges are imposed on the patient or third party payor for the extended upgrade functions, but considerably less than the cost of a replacement device and a surgical implant procedure, while converting the implanted device from an initially inexpensive and basic form to a more sophisticated form tailored to appropriate treatment and monitoring of the patient's condition.

30 Claims, 3 Drawing Sheets

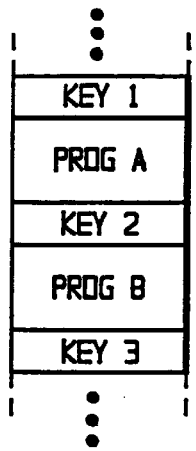
FIG. 4A
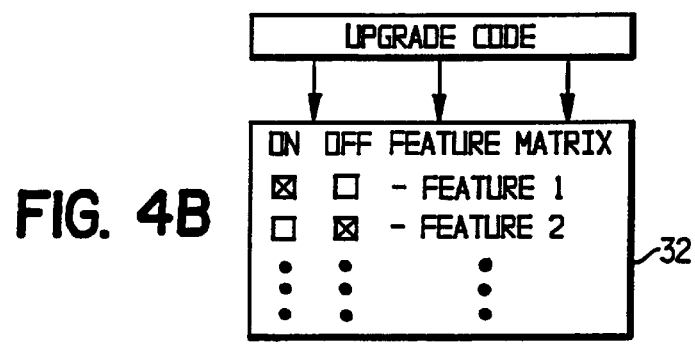
FIG. 4B
FIG. 4C
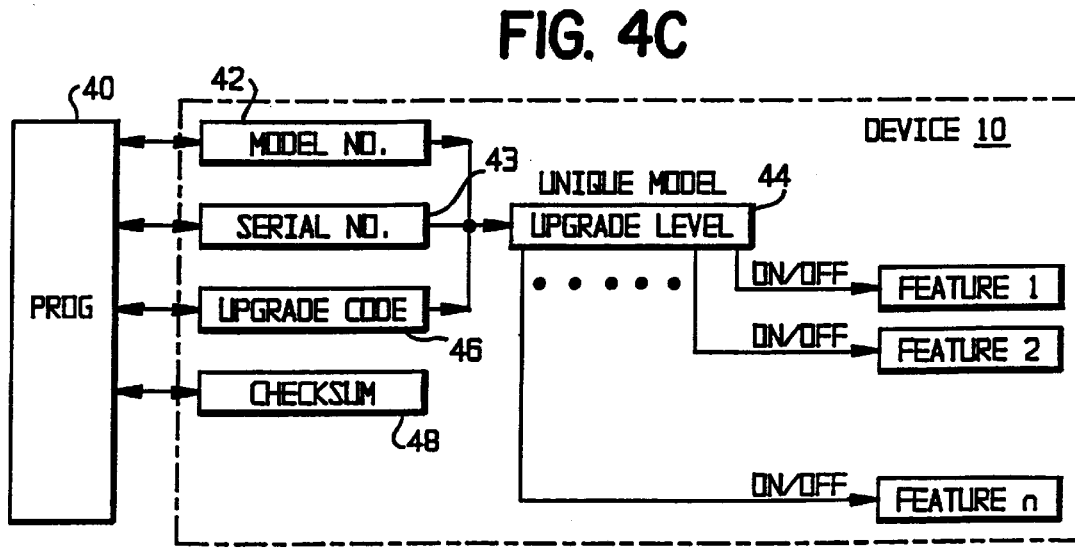

PROGRAMMABLY UPGRADABLE IMPLANTABLE CARDIAC PACEMAKER

CROSS-REFERENCE TO RELATED APPLICATION

This application is a continuation-in-part of co-pending application Ser. No. 08/648,707, filed May 16, 1996, now U.S. Pat. No. 5,725,559 (the "'707 application"), in the names of the same inventors and assigned to the same assignee as the present application.

BACKGROUND OF THE INVENTION

The present invention relates generally to implantable medical devices, and more particularly to a cardiac pacemaker which has a capability to be upgraded or modified non-invasively while surgically implanted, through remote programming.

Artificial cardiac pacemakers are typically implanted to control or correct an abnormality of the natural pacing or conduction system of a patient's heart. In general, the implanted pacemaker delivers an electrical pulse of selected magnitude to a predetermined location in the right atrium or ventricle to stimulate and pace the heart at a desired rate. Cardiac pacemakers for treating bradycardia and various other arrhythmias have evolved from the most simple asynchronous type in which the heart is paced at a fixed rate without sensing and thus without regard to the rhythmic relationship between the pumping chambers or the particular physiological requirements of the patient; to the synchronous type in which an event within the electrical activity of the heart is sensed and, depending on demand, a pulse is delivered (triggered) or not delivered (inhibited) at a fixed or base rate which takes into account the synchrony between the atrium and the ventricle; and finally, to the rate-adaptive or rate-responsive type that senses a physiological event which is indicative of the hemodynamic or metabolic demand of the patient, and delivers pacing pulses at a rate based on that demand as indicated by the nature and extent of the patient's physical activity (engaged in exercise) or lack thereof (merely at rest). An anti-tachycardia pacemaker is selected where the patient is suffering from episodes of an abnormally rapid irregular heart rate, and serves to break or terminate the tachycardia by delivering pulses to the appropriate chamber, typically the right ventricle, which are precisely timed relative to cardiac activity.

Various pacemaker codes have been devised, the original three letter ICHD code being perhaps most notable, to classify pacemakers according to function. The first letter is indicative of the chamber paced (atrium: A, ventricle: V, or both atrium and ventricle: D (for dual or double)); the second, the chamber sensed (A, V, D, or O—the latter indicating no sensing); and the third, the mode of response (triggered: T, inhibited: I, dual: D (for atrial triggered, ventricular inhibited), or none: O). Thus, for example, the outmoded DOO pacemaker was an atrioventricular (AV) synchronous sequential device in which both chambers were paced (D, the atrium at a constant rate and the ventricle at a fixed interval—the AV interval—thereafter), neither chamber was sensed (O), and the response mode was neither triggered nor inhibited. In another example, the VVI mode is ventricular inhibited—the ventricle is paced, but only if a naturally occurring R wave does not occur within a set time interval (the occurrence or lack of occurrence being determined by ventricular sensing), and otherwise the pacing pulse is inhibited. Yet another example is the DDD mode, in which both chambers are paced as well as sensed, atrial pacing is inhibited when either atrial activity or ventricular activity is sensed, and ventricular pacing is triggered when atrial activity is sensed. The addition of R as a fourth letter of the pacemaker code, e.g., VVI-R or DDD-R, is indicative of a rate-adaptive capability added to the basic mode.

Selection of the appropriate pacemaker to be implanted is made after the patient has been evaluated, the disorder (e.g., dysrhythmia) diagnosed, and a determination made by the cardiologist that pacing with an implanted pacemaker will provide effective therapy to treat and alleviate the dysrhythmia. As with any therapy, consideration of side effects and contraindications is vital. The techniques of selecting the respective proper pacing modes for treating particular dysrhythmias have been presented in algorithmic form; for example, by M. Schaldach in 1992 (see *Electrotherapy of the heart,* Springer-Verlag, Berlin (1992)).

For many patients, the progressive nature of cardiac disease necessitates upgrading the patient's implanted pacemaker to accommodate a change in the patient's condition. Typically, this is done by surgically removing what has become a less-effective or ineffective device and implanting a new pacemaker which can provide effective treatment for the existing dysrhythmia. In U.S. Pat. No. 5,609,613, issued Mar. 11, 1997 ("the '613 patent") to the same assignee as that of the present application, improvements are disclosed in artificial pacing for various conditions of patient rest, exercise/activity, and atrial dysrhythmia, and with the advantage of automatic mode switching between dual-chamber and single-chamber modes. Introduction of the fully automatic DDD pacemaker had enabled several clinical aims to be achieved, including adapting ventricular pacing rate to depend on rate of the sensed intrinsic atrial signal, and AV synchrony, but it was subsequently found that some 50% of the DDD pacemaker implant patients were experiencing atrial sensing problems or atrial instability, with underlying atrial rhythm disorders. For those patients, it became necessary to switch from the DDD mode to the simpler VVI mode, by pacemaker replacement. Subsequent improvements in sense amplifiers, electrodes for atrial leads, and timing cycles (e.g., dynamic AV delay and refractory periods) gave DDD pacemakers the capability to provide effective therapy to some of these patients, but a considerable percentage with the dual chamber implants still suffered from inadequate atrial rates. It is estimated that one-third of all patients with sick sinus syndrome (characterized by sinoatrial (SA) arrest or SA exit block) have overly high atrial rates accompanying atrial fibrillation, atrial flutter, or sinus tachycardias including atrial reentry tachycardias and ectopic tachycardiac events (which develop from a focus other than the SA node), as well as slow heart rates.

Proposals have been advanced to discriminate between physiologic and pathologic atrial rates in dual-chamber pacemaker-implant patients for use in switching the pacing mode from an atrial-sensing, ventricular-tracking DDD or VDD mode to a pure ventricular stimulation mode such as VVI or VVI-R. In VVI mode, since pacing and sensing functions take place in the ventricle only, an absence of sensed depolarizations within a set period results in pacing at a programmed nominal rate, and if spontaneous depolarizations are sensed at a faster rate, the pacing pulse is inhibited. But if the atrial detection rate for mode switching is set too low, physiologically-increased atrial rates attributable to physical exercise can cause reversion to an inappropriately low rate; and if the inappropriately high atrial rate detection criterion is set too high, atrial rates occurring with slow atrial flutter, sinus tachycardia, or ectopic beats may be lower and result in overly high ventricular rates despite a resting patient.

To prevent a DDD mode response to an inappropriate high atrial rate by pacing the ventricle at an equally fast rate, the pacemaker is usually programmed with a maximum pacing rate (MPR, or upper rate limit) to produce an abrupt 2:1 AV block. Pacing at the MPR would be undesirable when the patient is inactive because of a tendency to develop symptoms of cardiac insufficiency, lung congestion, shortness of breath, and angina pectoris, under conditions of high myocardial oxygen consumption, particularly if the patient suffers from coronary stenosis. Moreover, the abrupt 2:1 block can cause an undesirable abrupt change in cardiac output and blood pressure, even where high atrial rate is appropriate under conditions of patient exercise. Total atrial refractory period (TARP, which is the sum of the AV interval and the post-ventricular atrial refractory period or PVARP) allows an atrial rate to be reached where sensing of atrial beats cannot occur because they fall in the atrial refractory period.

Rate-adaptive pacing techniques are used to monitor artificial pacing rate and intrinsic heart rate, as well as for controlling the pacing rate to meet the patient's metabolic needs. Proposed sensing for this type of pacing has included central venous blood temperature, QT-interval detection, minute ventilation, intracardiac impedance, and motion detection. For example, the RELAY™ dual-chamber, multiprogrammable, accelerometer-based rate-adaptive cardiac pulse generator manufactured by Sulzer Intermedics Inc. (Angleton, Tex.) not only varies the pacing rate according to the patient's level of activity (or lack of activity, i.e., resting) and body position but also monitors the adequacy of triggered pacing of the atrium. (RELAY is a trademark of Sulzer Intermedics Inc.).

In the RELAY™ pacing system the MPR is supplemented by a slower interim rate which is greater than the lower rate limit of the device—a ventricular tracking limit (VTL)—to which the pacing rate moves from its base rate conditioned on a high atrial sensed rate without patient exercise. This conditional VTL (CVTL) may be programmed "on" (i.e., as an operating condition of the device) to undergo a controlled jump to the interim rate when a high intrinsic rate is sensed in the atrium without confirmation of patient exercise from the accelerometer. CVTL is overridden when MPR is programmed "on" and the rate calculated from patient exercise exceeds the programmed base pacing rate by a preselected amount—20 bpm, for example. At this accelerometer-based rate threshold, the pacemaker pulse generator restores 1:1 AV synchrony up to the MPR.

The '613 patent discloses a rate-adaptive, dual chamber pacemaker in which the VTL is a dynamic rate, and the ventricular pacing rate is controlled through several different rate zones, based on a combination of (i) dynamic adjustment of VTL according to the accelerometer-based activity signal, and (ii) automatic mode switching from a dual-chamber to a single-chamber mode with reversion to the dual-chamber mode based on an atrial cut-off rate and a programmable rate criterion. Among other things, a mode switch rate (MSR) is designated—above the MPR—that represents an atrial rate unlikely to be exceeded by even a healthy person with a normal cardiovascular system. In one embodiment of that invention, mode switching from DDD-R to VVI-R takes place automatically when the sensed atrial rate exceeds the MSR for a programmed number of consecutive cardiac cycles ranging, for example, from one to seven; and reversionary mode switching reversion back to dual-chamber operation occurs automatically when the sensed atrial rate falls below the MSR for one cycle.

While automatic mode switching is desirable in cases which are amenable to that function to avoid a need for physician reprogramming, there are instances in which progression of cardiac disease mandates a more permanent change in device functionality, or additional features not previously required for control of the patient's dysrhythmia. In the '707 application, an implantable defibrillator having capabilities of artificial pacing, cardioversion and defibrillation is made to be upgradable non-invasively by programming and re-programming the device in a secure manner each time the patient's condition undergoes a significant change, to provide the minimum functional capabilities required to treat the patient's current dysrhythmia, thereby enabling the patient or third party insurer to avoid costs of device features, which, although available in the device, are not presently being used, and of related implant surgical procedures.

It is a principal aim of the present invention to provide an implantable cardiac pacemaker which may be programmed in a secure manner to provide a non-invasive change in basic operating modes when the physician's diagnosis indicates a need for such change to treat a then-current condition. Changes contemplated by the present invention to be available by such programming of the pacemaker include changes from single to dual chamber operation, and addition of features or functions such as anti-bradycardia pacing therapy, anti-tachycardia pacing therapy, and rate-adaptive pacing therapy, and extended memory to record and store intrinsic physiological signals of the patient and their trends over time, such as heart rate and ECG morphology, respiration and other indicators from which to diagnose congestive heart failure and of a special condition of the patient.

Another aim of the invention is to provide an implantable pacemaker which has various therapeutic features and capabilities, some of which may be activated for initial treatment of a patient's pacing problem and others of which can be rendered inactive or disabled for the time being and subsequently selectively made available from time to time only if and when prescribed for treatment of an advanced stage of progressive cardiovascular disease, without a requirement of surgical removal and replacement of the implanted device. Initially, the cost to the patient for the device can be relatively low, limited to that level which is appropriate for the limited features of the device which have been activated. As additional features are activated when needed in the course of treatment of an advancing disease, additional charges may be imposed to allow recovery of costs of development, manufacture, distribution and marketing associated with those features.

SUMMARY OF THE INVENTION

According to the invention a programmable multi-mode cardiac pacemaker electrical function generator is adapted to be implanted in the body of a patient and to be upgradable from time to time to enable the device to provide appropriate treatment of arrhythmias attributable to abnormalities in the pacing or conduction system of the patient's heart as the needs of the patient for such treatment undergo change. In a presently preferred embodiment, the function generator includes means for providing a plurality of different pacing therapy modes in which electrical phenomena are produced for selective application to the patient's heart to treat arrhythmias, as well as other functions such as extended memory and diagnostic modes referred to above, and means for selectively enabling the mode/function providing means to operate in at least one of the therapeutic modes selected to produce electrical phenomena designated to treat a diagnosed arrhythmia of the patient or to provide such other functions as the memory and diagnostic modes. Means are provided for selectively sensing the patient's atrial and ventricular electrical activity, and the generator includes means responsive to detection of the occurrence of the diagnosed arrhythmia from the sensed atrial and/or ventricular activity for producing the designated electrical phenomena.

According to an important feature of the invention, the generator is programmable to non-invasively disable those of the pacing therapy modes or the memory and diagnostic modes which are not required to produce the designated electrical phenomena, and means are provided for selectively restoring disabled modes, and for precluding such selective restoration except upon access through a security code. The pacing therapy modes available in the device may include anti-bradycardia, anti-tachycardia, and rate-adaptive pacing; and both single chamber and dual chamber paced, sensed and response modes may be selected for treating bradycardia.

The memory modes and diagnostics include acquiring real-time ECG morphology of intracardiac and surface leads, the trend of this information over time, and the activation of the memory or a Holter function in conjunction with certain events. Such events include, for example, mode switching from DDD to VVI-R under the condition of inappropriate atrial dysrhythmias such as atrial fibrillation. If at the time of implant the patient exhibits a stable sinus rhythm, the physician may decide that it is unnecessary to enable the function of internal memory to record and store this type of information, and to make it available later by telemetry transfer. Then if the patient's condition warrants at some later time, following an examination of the patient by the physician or from events reported by the patient to the physician, the functions of the implanted device may be upgraded to include this function by programming the device through use of a special access key and imposition of additional charges on the patient's account to compensate the device manufacturer for the extended function. When such features are activated and the related information is made available to the physician it is very useful for diagnostic purposes and subsequent fine tailoring of the specific functions of the implanted device to the patient's individual needs.

The same considerations apply to recording of physiological signals indicative of congestive heart failure, from which the attending physician may better evaluate the patient's condition and adjust a therapeutic regimen such as water pills, ACE inhibitors, or specific device functions such as pacing rate or mode of operation. As in the case of other extended memory functions, the patient might not be suffering from congestive heart failure at the time of implant, but may be observed to have developed this new condition over time. Again in this case, by upgrading the implanted device through programming which may include software transfer and hardware activation, with use of the special access key plus additional payment for the upgrade function, an initially simple and inexpensive device is converted to a more sophisticated device without subjecting the patient to additional surgery.

At least some of the pacing therapy operational modes would be disabled by the physician at the outset, for restoration only when and if the patient's needs mandated the provision of a new treatment. But to avoid the possibility of an unauthorized upgrade or an upgrade without appropriate charge to the patient's account to allow cost recovery by the manufacturer, a security code or key supplied by the manufacturer is mandated to allow the desired mode restoration. The pacemaker generator may be implemented to allow restoration of a selected mode in response to any of several distinct and different security codes which are unique to the particular implanted device, where each of the security codes is supplied by the device manufacturer. Alternatively or additionally, each the security codes may be associated with a respective distinct and different mix of enabled and disabled pacing or functional operating modes, so that a particular mix is available only with a specific one of the codes.

The generator may also include means for automatic mode switching from DDD to VVI pacing when the sensing circuit detects a pathologic atrial tachyrhythmia and for automatic reversion to DDD from VVI when the sensing circuit detects a physiologic atrial tachycardia, without interfering with or otherwise affecting these features of the implanted pulse generator, i.e., where the automatic mode switching is distinct from the mode providing means of the device.

According to a preferred embodiment of the invention, a solution to the problem is effected by providing a basic implantable artificial cardiac pacemaker which although it may be and preferably is capable of providing a variety of different cardiac arrhythmia or dysrhythmia therapies that address pacing abnormalities or electrical conduction disorders of the heart—for purposes of this summary is considered (at least initially) merely from the standpoint of its capability to deliver stimulating pulses, including single pulses, multiple pulses, trains of pulses, and pulse bursts to the patient's heart (characterized herein as "stimulating pulses"). The stimulating pulses are derived from a pulse generator, and, ideally, are effective to provide the desired pacing or conduction therapy to the heart and to return the heart rate to normal sinus rhythm.

For many cardiac pacemaker patients, the conditions sought to be treated by the implant may consist not only of, say, bradycardia, but may include other cardiac problems which had previously been successfully treated with a particular mode of cardiac stimulation which is no longer effective because of advanced disease of the patient. The situation requires a more aggressive therapy, or an adjunct therapy, such as VVI-R rate adaptive pacing, in order to improve an underlying cardiac hemodynamic condition as well.

If a patient exhibits a particular condition or event, it would be desirable to activate otherwise disabled Holter monitor and memory functions by programming the device accordingly, so as to enable a more exact analysis and diagnosis to be made by the physician from which to prescribe a new or adjusted therapy to be delivered by the device which is more tailored to the patient's needs. A cardiac patient does easily tolerate the physical, mental, emotional, and economic toll of multiple operations which may range from an initial relatively simple implant device to successively more complex devices to meet the advancing needs for therapy dictated by progressive heart disease. Added to this is the care required to be delivered to this patient by the physician, surgical, and hospital services, and, where care may be limited by government-imposed cost containment mandates, as it is with the very patients of advanced years who generally have need for such implant devices, the situation becomes particularly difficult.

It is therefore another important aim of the present invention to provide an implantable full featured cardiac pacemaker which is capable of delivering a full range of pacing therapies, from the patient's needs at onset of the disease through progressively more serious pacing anomalies and conduction disorders that often accompany advancing age. According to the invention, the implanted device is programmed and reprogrammed only as and to the extent that it becomes necessary to meet those needs. Although the pacemaker is full featured, the patient (or third party payor, if applicable) need make no initial financial outlay for the device itself beyond that required to cover the pricing for those features of the device which are made available at the time of implant according to the physician's current prescription. Thereafter, additional device charges are imposed only to the extent that additional features are prescribed and programmed to treat an advancing disease or new disorder. Accordingly, the patient's account is not addressed for features which, though available within the device itself by proper programming, are presently unused and not a part of the device-implemented therapy provided to date.

Initially, then, at the time of implant the pacemaker need merely be made capable of performing the basic pacing therapeutic needs required by the patient. The basic needs may, for example, include or be limited to the delivery of a pacing function required to treat a type of bradycardia currently suffered by the patent, along with a Holter monitoring function. However, the device possesses means that enable it to be programmably upgraded non-invasively and successively, whenever the requirement exists for additional therapy(ies) to be delivered to meet the additional needs of the patient if, when, and as they may arise with the passage of time. In essence, this means that the hardware and software routines for the full range of initial and additional intelligent pacing functions are present in the device, with the software control parameters necessary to configure a specific functionality ready to be programmed at any time. And although access to previously restricted software and hardware features would impose additional charges, the cost would be only a fraction of that required for the alternative of multiple surgeries for replacements.

It is necessary, however, to provide a way in which the capability to program the device for new features is restricted only to authorized persons, such as the patient's attending cardiologist. To that end, the device is encoded in a suitable manner to lock it against (i.e., deny) access to those of its internal programs which relate to upgrades, which may be a change, addition, or even selective removal of therapies, except to one having a key to unlock the access. The key(s) to unlocking the code is supplied by the pacemaker manufacturer, or the necessary programming changes could be made from time to time by the manufacturer by telephonic data transmission or by representatives located at the -treatment centers, when a new or different therapy regimen is prescribed by the patient's physician. In any event, those functions which have customarily been made programmable in conventional implanted devices to allow changes, selections, activation, or deactivation by the physician (or in some cases, by the patient, as well) need not be affected, so that such programming could be performed in the usual manner without need for the special codes or keys that mark the security for an upgradable device. To obtain the security code or key necessary to upgrade the device, a payment is required in an amount that reflects the nature of the upgrade. For example, the amount of the payment may be based on the number of additional device functions which will become available from the upgraded device.

According to a further aspect of the invention, upgrading may be performed by identifying the serial number of the device to allow a certain code to be addressed by programmer software. For example, a very fast upgrade of a particular patient's device so identified uses data supplied by the device manufacturer by an available data communication technique to activate otherwise dormant (through blocking) additional functions.

BRIEF DESCRIPTION OF THE DRAWINGS

The above and still further aims, objects, aspects, features and attendant advantages of the present invention will become apparent from a consideration of the following detailed description of the presently contemplated best mode of practicing the invention, by reference to a preferred embodiment and method, taken in conjunction with the accompanying drawings, in which:

FIGS. 4A, 4B, and 4C are functional block diagrams useful in further explaining the preferred embodiment of a device implemented according to the invention, and the preferred method of providing pacing therapy using the device.

DETAILED DESCRIPTION OF THE
PREFERRED EMBODIMENT AND METHOD
OF THE INVENTION

Figure 1:
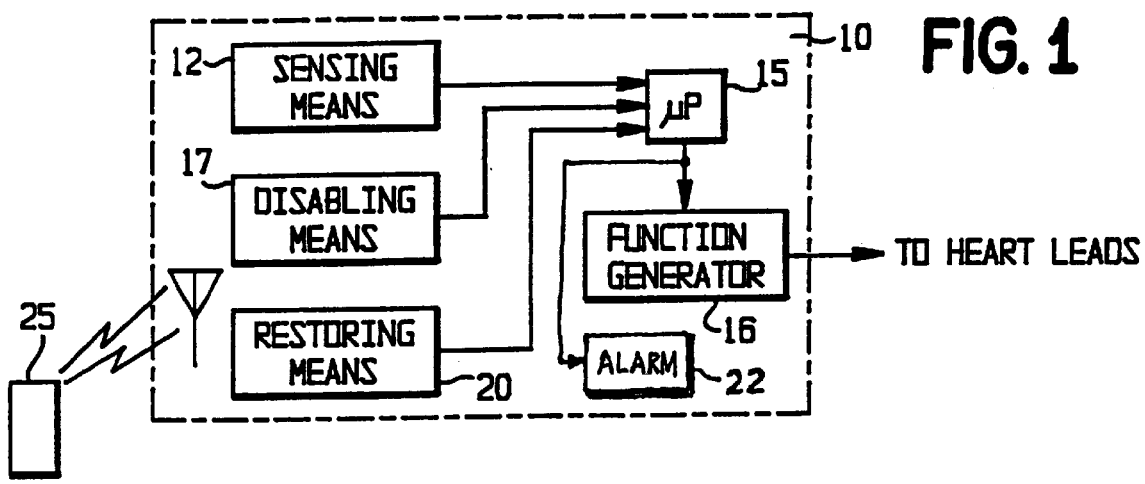
FIG. 1 is a block diagram of an implantable pacemaker embodying the concepts and principles of the present invention.

FIG. 1 is a block diagram of an exemplary embodiment of an implantable pacemaker 10 equipped according to the invention. All components of the device may be entirely conventional except as otherwise described herein. The pacemaker is adapted to be upgraded from time to time after implant as necessary to enable it to provide additional pacing therapy with the changing needs of the patient.

The device 10 includes a function generator 16 which includes a conventional pulse generator implemented with multiple pacing operational modes corresponding to a continuum of electrical pulse stimulation therapies and monitoring capabilities to treat various diagnosed pacing and electrical conduction disorders (i.e., arrhythmias or dysrhythmias), and various separate extended memory and diagnostic functions. The stimulation therapies are characterized by various types of relatively low energy pulses or pulse waveforms for anti-bradycardia, anti-tachycardia and/or rate adaptive pacing therapy, to be delivered to the patient's heart through conventional implanted leads and electrodes. The electrodes may include the biocompatible metal housing (i.e., the case, or "can") of the pacemaker as an active electrode.

Pacing functions of the pulse generator are performed under the control of a single-chip microprocessor ($\mu$P, typically, of semiconductor integrated circuit form) unit 15 with conventional arithmetic, logic, and control capabilities and associated memory capacity, which enable it to respond to a multiplicity of programmed instructions and sufficiently powerful to run programs at high speed in real time. On-chip or off-chip (i.e., internal or external to a semiconductor IC die or chip) program and data memories are used in conjunction with external telemetry programming equipment and related software or firmware to enable device functions to be modified or replaced by an authorized person.

Sensing means 12 although shown for the sake of convenience as being within the enclosure of the device 10, includes electrodes associated with the same heart leads to which the output of the function generator 16 is applied, and implanted within the respective chambers of the heart to detect cardiac activity and generate signals indicative of the patient's electrocardiogram (ECG) including heart rate and rhythm. The sensing means also includes an accelerometer or other physical activity/exercise sensor within the housing (or within its own separate housing that may be implanted in the patient's body) which enables the pacemaker to provide a rate adaptive response to the status of patient activity in conjunction with the other artificial pacing functions. Also included in the sensing means 12 are conventional sensors implanted in the patient to detect physiological signals useful, for example, for detecting congestive heart failure. Signals generated by the sensing electrodes and the other sensing means are converted to digital form and supplied to microprocessor 15 for appropriate control of the pulse generator. The microprocessor responds to each different arrhythmia and other relevant physiological parameters detected by the sensors to enable the function generator to generate an output pulse waveform (or a sequence of waveforms according to a predetermined hierarchy) for treatment of the detected arrhythmia.

When no immediate demand for therapy has been imposed on the pacemaker for a predetermined time interval, an interrupt signal is generated and the microprocessor reverts to a "sleep" mode, subject to be awakened at any time that a therapy requirement exists, such as by the sense signals indicative of an arrhythmia.

According to a feature of the invention, disabling means 17 are provided for programmably disabling at least some of the multiplicity of therapy functions or modes that are otherwise available from the implanted pacemaker. The therapy modes themselves are all entirely conventional. A principal distinction of this pacemaker device from the prior art, however, is the provision of the means by which its capability to deliver all of the therapy modes may be intentionally curtailed (or restored) by an authorized person. Nevertheless, the device is left with at least one therapy mode (or as many as are necessary to treat the current diagnosed condition of the patient) intact and ready to be delivered to the implant patient's heart, according to the prescription of the attending physician. Programming is performed by telemetry using a remote programmer unit 25 (which may have an associated wand, not shown) in conjunction with an antenna and circuitry located within the device housing 10.

For example, if the patient is experiencing sporadic pathologic tachycardia, but no other manifestations of cardiac pacing or conduction disorders, the implanted device would be programmed to deliver an anti-tachycardia therapy. This may include, for example, a number of different pulse waveforms (e.g., selectively timed single pulse, pulse train, pulse burst(s)) that are delivered in a hierarchical sequence or regimen ranging from a conservative response to a relatively aggressive response, with suspension of the regimen at any point at which the tachycardia is broken, but restricted to that dysrhythmia. A feature of the device is that in the event all therapy modes are inadvertently disabled by the programming person, a signal (e.g., audible) is generated by the programmer unit (and/or internally within the implanted pacemaker, e.g., to excite the patient's pectoral muscle, as indicated by alarm 22) together with a message to that effect on a visual (e.g., liquid crystal) display of the programmer unit, as a warning of the need to correct that situation.

If the device to be implanted had been implemented for only a single therapy mode—say, the anti-tachycardia therapy of the preceding example—without a capability to be upgraded with other therapy modes as a need arose, the cost to the patient or third party insurer of the device and the implant procedure would not be substantially different, and likely not less, than that which would be incurred for implantation of the multi-mode pacemaker of the invention, for this initial function or therapy. This excludes any additional costs that might be imposed for differences attributable to the implant location in the patient's body, and nature and number of heart leads and other leads and sensors required to be implanted. But in the case of the single mode device, the patient's need for additional pacing or pacing-related therapy(ies) as a result of progressive heart disease would necessitate explanting the current device for replacement with a device capable of providing these newly required therapies. Not only would the patient's account be charged for the additional cost of the new device and of the surgical procedure required to implant it, but the patient would suffer the trauma and risk of the new surgery—regardless of the relatively routine nature of the procedure.

In contrast, the pacemaker of the present invention is provided with restoring means 20 for selectively restoring some or all of the disabled functions through the use of the programmer unit 25, while leaving the previous working therapy mode(s) intact or disabling it (them) through appropriate programming of the disabling means 17. As will be described presently, security means are provided for encoding the device to preclude restoration of disabled functions (or any other modification of device features), except by an authorized entity. In the preferred embodiment, the security means is implemented to require participation by both the attending physician and the device manufacturer to effect an upgrade. Hence, by implanting such an upgradable pacemaker, the patient's need for additional or different pacing therapy modes attributable to progressive heart disease is readily accommodated by simply programming the implanted pacer to upgrade its features accordingly.

It is desirable that a pacemaker with this capability for programmable upgrading should be sufficiently secure to render it virtually incorruptible. To that end, the device is provided with a security system to prevent it from being reprogrammed without an appropriate key or keys, as described below. It is also important that the upgradable device be compatible with existing applications in the field, so that it will not be susceptible to interference or override from use of existing or future programming of device operation available from the pacemaker manufacturer. Preferably, each upgradable device has its own unique personal identification code, or identifier (ID) which is embedded in its nonvolatile memory so that the ID will not be erased in the event of a loss of electrical power to the pacemaker (which, of course, is provided by battery).

A compatibility determination check (i.e., to assure compatibility between the upgradable device and the external programmer, particularly with respect to software of each) may be performed by retrieving or verifying the nonvolatile ID (such as the serial number of the device) plus a volatile ID (such as the model number of the device). The volatile ID is embedded in programmable memory to allow it to be reprogrammed in the event of corruption. In addition to these ID's, a data memory of the device has a location which identifies the level at which the device is currently upgraded (i.e., the enabled features), based on the state of the device software. Thus, the upgrade level may be read at any time by the attending physician to verify the current status of the device; and may be written to in order to reprogram the device to a new upgrade level. An error detection code is provided, which can be read to detect errors, and written to correct errors. These techniques are provided or performed in a conventional manner, the uniqueness residing in the purpose for which they are used.

Also, in the preferred embodiment, the device is implemented with a backup reset to a full-featured pacemaker from a partial-featured mode, that requires programming of an authorized upgrade code at a later date for all features to remain active. Alternatively, the device may be reset to a predetermined limited functional mode, and prompts the user to obtain upgrade codes from the manufacturer. Both options allow instantaneous restoration of critical feature for patient safety, while preventing unauthorized upgrading. Only the most significant modes or functions that could affect the patient's life or safety under certain conditions, such as bradycardia backup pacing and anti-tachycardia pacing, need be restored by a reset module. Upgrading to provide the additional features is achieved only with special access module coded programming, which is activated by the manufacturer's acknowledgment tag of actual or commitment to payment of the applicable upgrade fee.

Figure 2:
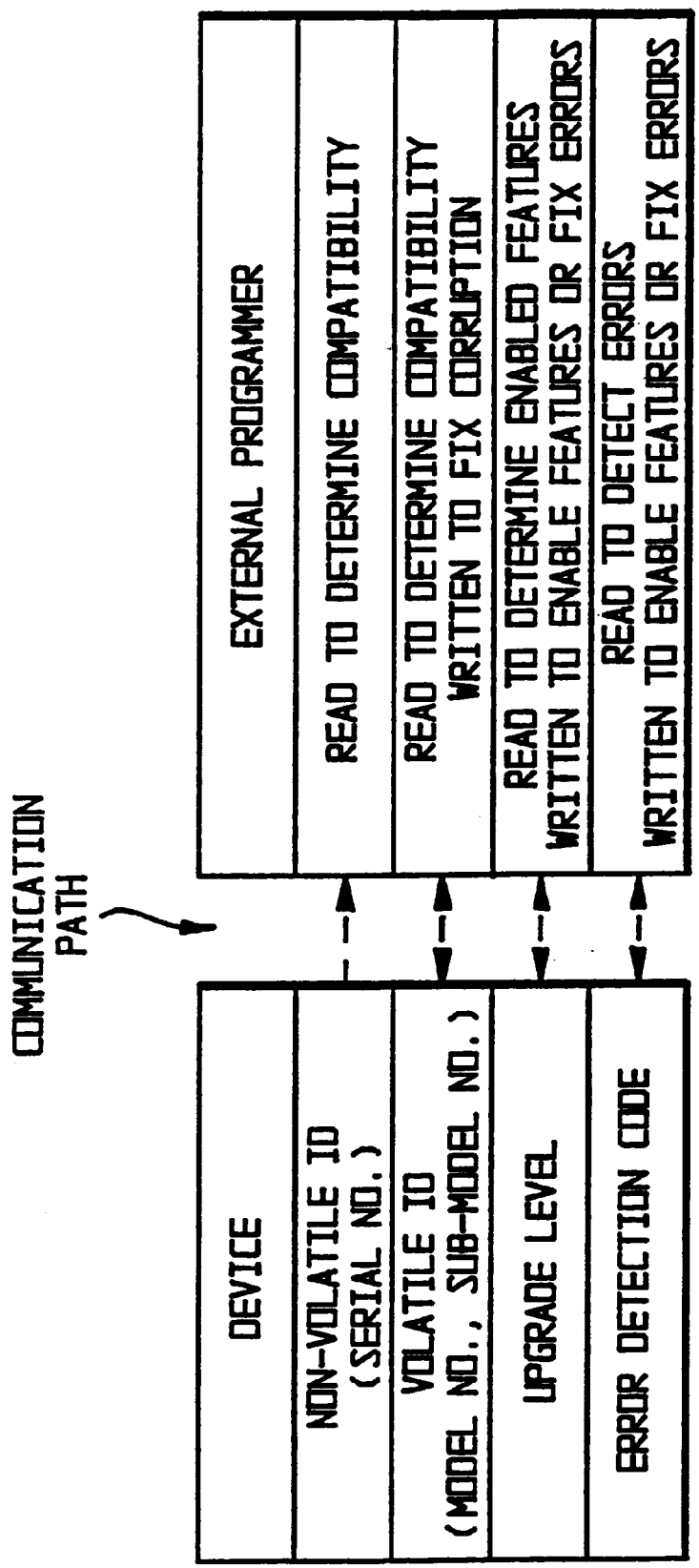
FIG. 2 is a chart of characteristics for the pacer of FIG. 1, and capabilities of an external programmer for accessing and programming memory of the device.

The capabilities of the preferred embodiment of pacemaker 10 are illustrated in the chart of FIG. 2. Device characteristics (such as those which have just been cited in the above example) are listed on the left, external programmer unit aspects are listed on the right, and direction of communication is indicated by arrows between the two. All of the listed pacemaker characteristics/parameters are stored in read-only memory (ROM) and random access memory (RAM), preferably on-chip. Device software supports the full range of features available, with all combinations of upgrades. The external programmer unit uses control parameters of the device software to enable, disable, or limit the range of features according to the selected upgrade level.

In the embodiment portrayed by FIG. 2, the serial number of the implanted device can be read only, to assess what therapy modes are accessible from the device and to determine its compatibility with various other applications available at the time. The model number is also readable, but can be rewritten if it (e.g., the data which identifies it) has been corrupted. The current status of the device (i.e., its present upgrade level, as defined by what therapy mode(s) implemented in the device are currently operating either by not having been programmably disabled or by having been restored after being disabled) is readable to determine which features (i.e., therapy modes) are currently enabled to treat dysrhythmias or to accommodate changes in operation toward such treatment. The upgrade level itself can be revised by programming to remove disabilities, and thereby install a new upgrade level, or to correct errors. Lastly, an error detection code is readable to allow errors to be detected, and is writable to allow any such errors to be corrected and features to be enabled.

Figure 3:
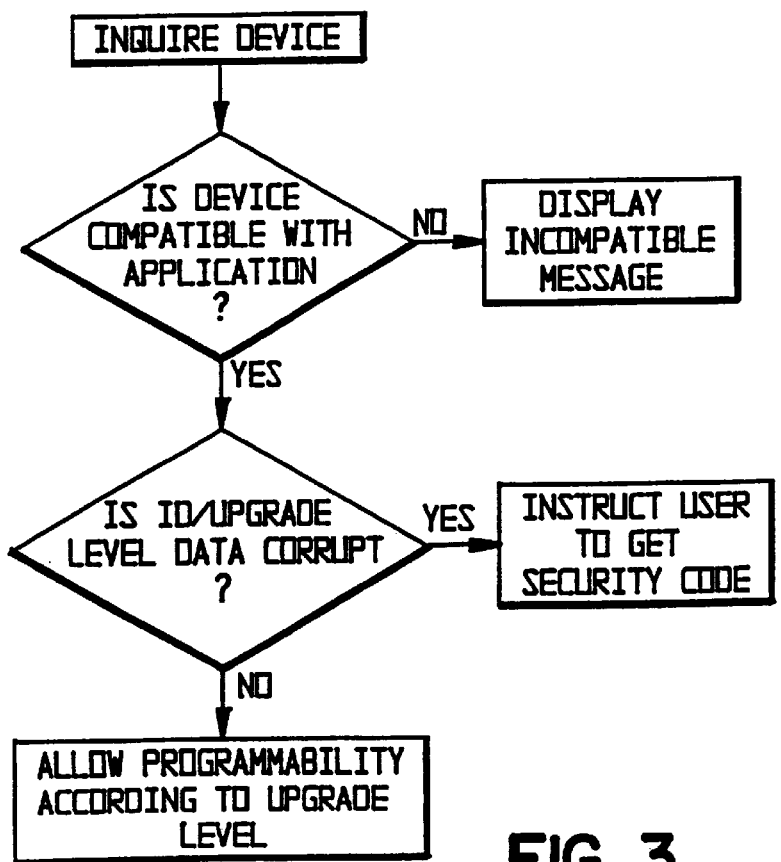
FIG. 3 is a flow diagram for the external programmer application software.

A flow diagram for the external programmer unit's application software is illustrated in FIG. 3. An inquiry is made to the pacemaker from the external programmer unit (i.e., the programming console) by appropriately positioning a wand associated with unit 25 (FIG. 1) in proximity to the pacemaker, to enable the device ID (serial number) to be read and to determine from it the compatibility of the device with the application software of the remote programmer unit. If compatibility does not exist, a flag or message is displayed to that effect on a display of the programmer. But if the two are compatible, a further test is made to determine whether the ID/upgrade level data have been corrupted. If so, the user (e.g., the physician or other authorized person) is instructed to get the security code. Otherwise, the user is notified (also on the display) that programming is permitted to the extent of the upgrade level. That is, while certain aspects of the therapy mode(s) available within that level of upgrade of the pacemaker can be modified without need for a security code, the specific level of the upgrade cannot be changed (absent access by means of the security code). Certain features may be limited in range or availability.

FIGS. 4A, 4B, and 4C illustrate aspects of the external programmer unit's control over features of the pacemaker. In FIG. 4A, a security code constituting a key (e.g., key 1, key 2, key 3, etc.) is required to unlock each program and the feature associated with the respective program. In the preferred embodiment, the appropriate key (security code) in each instance is supplied by the device manufacturer, upon notification from the implant patient's attending physician that the device is to be reprogrammed to modify the original pacing therapy mode (or subsequently upgraded version) to meet the patient's current needs for cardiac dysrhythmia therapy. The modification is performed on a non-invasive basis by simply programming the implanted pacemaker via telemetry with the external programmer unit after the key has been inserted. By safeguarding the key, the device manufacturer is assured of being notified before any adjustment can be made to the features of the device. A charge may then be imposed for the additional feature(s) to compensate the manufacturer, including a reimbursement of costs associated with the original implementation. Nevertheless, the cost imposed on (i.e., charged to) the patient's account is considerably less than for replacing an implanted device, and without the risk and trauma of an associated surgical procedure.

In FIG. 4B, the status of each feature is controlled by the upgrade code, which includes the respective key and the program for that upgrade/feature. For example, as shown, a feature 1 is programmed "on", while a feature 2 is disabled to be "off". Other features may be left or restored to be "on" or disabled to be "off" as necessary to provide device capabilities meeting the patient's needs. A display 32 on the programmer monitor shows the feature matrix as currently programmed. An upgrade code (another key) is applied in FIG. 4B to allow feature 1 to be enabled (or restored), and to leave feature 2 disabled, so as to modify the operational capability of the pacemaker to upgrade it from one level to another, according to the prescription.

In FIG. 4C, the external programmer 40 interrogates the pacemaker 10 for its model number 42 and serial number 43, and, if the response indicates that the compatibility is positive, checks the upgrade level 44 of the device, and applies an upgrade code 45 to manage the availability of certain features defined by sections of the software, by restricting or allowing access with software keys. Insertion of the upgrade code enables the programmer unit to install or restore the additional features called for. A checksum operation 48 is performed by the programmer unit to detect and correct errors. Having unlocked a feature or features with the applicable key, those unlocked features among 1, 2, . . . n, may be programmed to be disabled or restored as necessary or desired to provide the features (the therapy modes) required to treat the patient's cardiac arrhythmias as prescribed by the attending physician.

In the preferred embodiment, the upgrade information is stored in software or semiconductor memory in the device, and is encoded to deter intentional alteration. This is accomplished preferably by storing a value which is a complex mathematical combination of the upgrade level, the device model number, and the device serial number, so that the upgrade level value stored is then unique for each device.

This upgrade information, along with the model and serial number information for the device, is protected by an error detection code. In the preferred embodiment, the error detection code is a checksum that allows the application program to recognize alteration or corruption of the serial number or the upgrade level. When an error is detected, the application displays the serial number and upgrade level correction screen on the console, to prompt the user to contact the manufacturer for a security code.

Preferably, the upgradable device is adapted from an existing conventional device design, with customized programmer software architectures that minimize changes to existing conventional programmer application code and device code. The graded upgrading may apply to each individual therapy mode and other functional mode of the pacemaker, so that each such function when programmed into the device carries with it the imposition of a charge to the patient's account. Such charges are imposed for each new function until the pacemaker is has reached its ultimate operational capability for the condition of the particular patient in which the device is implanted, i.e., the optimum range of its features are made available to the patient, after which no further charges would apply. Additional charges would apply, for example, to extended memory, VVI-R pacing (rate adaptive), VDD pacing, anti-tachycardia pacing, and other diagnostic and therapeutic features.

From the above description, it will be appreciated that the present invention goes beyond the use of an external programmer unit to provide data to preselected registers and RAM memory locations within an implanted pacemaker, which affect either the sections of software routines to be executed or the parameters to be used in that execution. The invention represents an enhancement extending to a method and system of managing the availability of certain sections of the software which constitute operational features of the device by restricting or allowing access to those features (through the applicable sections of the software) by means of software keys.

In summary, the implantable cardiac pacemaker of the invention provides a multiplicity of pacing therapy modes for treating various cardiac pacing or conduction disorders. Atrial and ventricular activity of the patient's heart are selectively sensed to detect dysrhythmias. Software enables non-invasive programming of the pacemaker to selectively enable operation in at least one of the therapy modes based on the diagnosed current needs of the patient, and all other therapy modes are selectively inhibited or disabled. The pacemaker is also adapted for non-invasive programming to selectively restore operation of any one or more of the inhibited modes when the patient is diagnosed with a new or related disorder requiring that therapy, but such restoration cannot be performed except with a prescribed key or security code.

Included in the various pacing therapy modes are combinations of single and dual chamber sensing, pacing, and electrical response functions for treating bradycardia and pathologic tachycardia, as well for providing rate-adaptive pacing using an accelerometer as an activity/exercise sensor. In addition, the multi-mode pacemaker of the invention may be programmed with memory modes and diagnostics that include acquisition of real-time ECG morphology of intracardiac and surface leads, and the trend thereof over time, as well as activation of the memory or a Holter function in conjunction with various events such as mode switching from DDD to VVI-R pacing when the patient is diagnosed to be experiencing episodes of atrial fibrillation. Preferably, the pacemaker is implemented to switch automatically from DDD to VVI pacing mode when a pathologic atrial tachycardia is detected, and to revert automatically from VVI to DDD operation when physiologic atrial tachycardia is sensed, these modes being distinct from the pacing therapy modes selected by programming the pacemaker.

The selective restoration of one or more of the disabled modes requires knowledge and use of respective ones of a plurality of distinct and different security codes unique to the particular pacemaker implanted in the patient. Each security code is supplied by the manufacturer of the implanted device, and may be a code associated with a respective distinct and different mix of enabled and disabled pacing therapy modes, so that once a particular mix is selected, the same code which permitted that selection cannot be used for selecting a different mix.

Thus, although a presently contemplated best mode of practicing the invention has been described herein, it will be recognized by those skilled in the art to which the invention pertains from a consideration of the foregoing description of a presently preferred embodiment, that variations and modifications of this exemplary embodiment and method may be made without departing from the true spirit and scope of the invention. Accordingly, it is intended that the invention shall be limited only by the appended claims and the rules and principles of applicable law.

What is claimed is:

1. A programmable multi-mode cardiac pacemaker device adapted to be implanted in the body of a patient and upgraded from time to time to enable the device to provide appropriate treatment of arrhythmias attributable to abnormalities in the cardiac pacing or cardiovascular system of the patient, as the needs of the patient for such treatment undergo change, said device comprising means for providing a multiplicity of different pacing operating modes in which electrical stimuli are produced for selective application to the patient's heart to treat arrhythmias; means for selectively sensing electrical activity of the patient's heart; means for selectively enabling said mode providing means to operate in at least one of said modes selected to produce electrical phenomena designated to treat a diagnosed arrhythmia of the patient; means responsive to detecting the occurrence of the diagnosed arrhythmia from sensed atrial or ventricular electrical activity for producing the designated electrical phenomena; means for programming said device to non-invasively disable those of said multiplicity of pacing operating modes which are not required to produce the designated electrical phenomena; and means for selectively restoring disabled pacing operating modes, including means for precluding said selective restoration except upon access through a security code.

2. The programmable multi-mode cardiac pacemaker device of claim 1, wherein said mode providing means is adapted to provide at least anti-bradycardia, anti-tachycardia, and rate-adaptive operating modes to treat arrhythmias.

3. The programmable multi-mode cardiac pacemaker device of claim 2, wherein said mode providing means is adapted to provide both single chamber and dual chamber paced, sensed and response modes for treating bradycardia.

4. The programmable multi-mode cardiac pacemaker device of claim 1, including means for automatic mode switching from DDD to VVI pacing when said sensing means detects a pathologic atrial tachyrhythmia and for automatic reversion to DDD from VVI when said sensing means detects a physiologic atrial tachycardia, wherein said automatic mode switching and reversion means is distinct from said mode providing means.

5. The programmable multi-mode cardiac pacemaker device of claim 1, wherein said means for precluding restoration is implemented to respond to each of a plurality of distinct and different security codes which are unique to the specific device implanted in the body of the patient.

6. The programmable multi-mode cardiac pacemaker device of claim 5, wherein each of said distinct and different security codes is a code supplied by the manufacturer of the implanted device.

7. The programmable multi-mode cardiac pacemaker device of claim 6, wherein each of said distinct and different security codes is a code associated with a respective distinct and different mix of enabled and disabled pacing operating modes, so that once a particular mix is selected, the same code which permitted such selection cannot be used for selecting a different mix.

8. The programmable multi-mode cardiac pacemaker device of claim 1, wherein said mode providing means is further adapted to selectively provide additional memory and logic functions to store and analyze events pertaining to malfunction of the patient's cardiovascular system and to the operation of the pacemaker in response thereto, for subsequent retrieval from the pacemaker by telemetry.

9. The programmable multi-mode cardiac pacemaker device of claim 1, wherein said mode providing means is further adapted to selectively perform a function of monitoring signals indicative of physiological parameters of the patient other than electrical activity of the heart, for subsequent retrieval from the pacemaker by telemetry.

10. The programmable multi-mode cardiac pacemaker device of claim 1, wherein obtaining said security code is conditioned upon payment for access to one or more additional ones of said pacing operating modes.

11. An implantable cardiac pacemaker for arrhythmia detection and correction, adapted to provide a multiplicity of different pacing therapy modes in the form of respective combinations of single and dual chamber sensing and pacing and rate-adaptive pacing of a patient's heart to correct any of various cardiac arrhythmias thereof attributable to cardiac pacing or conduction disorders, said pacemaker comprising means for making available said multiplicity of different pacing therapy modes; means for non-invasively programming said pacemaker to selectively enable current operation of at least one of the available pacing therapy modes according to current needs of the patient and to selectively inhibit current operation of all others of the available pacing therapy modes; and means for non-invasively programming said pacemaker to selectively restore operation of at least one of the inhibited pacing therapy modes, including means to lock out operation of the programmable restoring means except with a prescribed key.

12. The implantable cardiac pacemaker of claim 11, wherein said multiplicity of different pacing therapy modes includes combinations of single and dual chamber sensing, pacing, and electrical response functions for correcting bradycardia and pathologic tachycardia.

13. The implantable cardiac pacemaker of claim 11, including means for making available rate-adaptive pacing among said multiplicity of different pacing therapy modes, and an accelerometer for sensing physical activity of the patient to initiate the rate-adaptive pacing when the pacing mode therefor is selectively enabled for current operation.

14. The implantable cardiac pacemaker of claim 11, further including means providing the availability of memory and diagnostic modes in addition to said pacing therapy modes, by which to enable at least one of (i) acquisition of real-time ECG morphology of intracardiac and surface leads, (ii) trends of patient arrhythmias and treatment thereof over time, and (iii) memory functions for recording cardiac and pacemaker operating events.

15. A method for selectively non-invasively upgrading a programmable multi-mode cardiac pacemaker device adapted to be implanted in the body of a patient to enable the device to provide appropriate treatment of arrhythmias attributable to abnormalities in the cardiac pacing or cardiovascular system of the patient, as the needs of the patient for such treatment undergo change from time to time, said method comprising the steps of providing the device with a plurality of different programmable diagnostic, memory, and operating functional modes in which respective electrical pulse waveforms are produced for selective application to the patient's heart to treat arrhythmias; selectively sensing electrical activity of the patient's heart; programming the device to enable operation thereof in at least one of said functional modes selected to produce an electrical pulse waveform designated to treat an arrhythmia when diagnosed in the patient in response to detection of the occurrence of the diagnosed arrhythmia from sensed electrical activity of at least one of the atrial and ventricular chambers of the heart, while leaving those of said plurality of functional modes which are not required to produce the electrical pulse waveform designated to treat the diagnosed arrhythmia initially disabled; and selectively restoring one or more of said disabled functional modes when needed to upgrade the device, only upon access through a security code.

16. The method of claim 15, wherein said operating functional modes include anti-bradycardia, anti-tachycardia, and rate-adaptive pacing to treat arryhthmias.

17. The method of claim 16, wherein said operating functional modes include both single chamber and dual chamber paced, sensed and response modes for treating bradycardia.

18. The method of claim 15, including the steps of automatic mode switching from DDD to VVI pacing when said sensing detects a pathologic atrial tachyrhythmia and of automatic reversion to DDD from VVI when said sensing detects a physiologic atrial tachycardia, distinct from said modes selected by programming the device.

19. The method of claim 15, wherein the step of selectively restoring one or more disabled functional modes includes responding to each of a plurality of distinct and different security codes which are unique to the specific device implanted in the body of the patient.

20. The method of claim 19, wherein each of the distinct and different security codes is a code supplied by the manufacturer of the implanted device.

21. The method of claim 20, wherein each of said distinct and different security codes is a code associated with a respective distinct and different mix of enabled and disabled functional modes, so that once a particular mix is selected, the same code which permitted such selection cannot be used for a different mix.

22. The method of claim 15, wherein obtaining said security code to upgrade said device is conditioned upon payment therefor.

23. The method of claim 22, wherein the amount of said payment is based upon the number of additional functions enabled in the upgraded device.

24. A method of correcting any of various cardiac arrhythmias attributable to cardiac pacing or cardiovascular disorders of a patient with a programmably upgradable implantable cardiac pacemaker adapted for arrhythmia detection and correction by providing a plurality of different pacing therapy modes in the form of respective combinations of single and dual chamber sensing and pacing and rate-adaptive pacing of the patient's heart, said method comprising the steps of making available said plurality of different pacing therapy modes of the pacemaker; non-invasively programming the pacemaker to selectively enable current operation of at least some of said plurality of available pacing therapy modes according to current needs of the patient while inhibiting current operation of all others of said plurality of available pacing therapy modes; and subsequently non-invasively programming the pacemaker to selectively restore operation of at least one of the inhibited pacing therapy modes when the patient evidences a need therefor, including locking out the capability to programmably restore operation of an inhibited pacing therapy mode except with a prescribed key.

25. The method of claim 24, wherein said plurality of different pacing therapy modes includes combinations of single and dual chamber sensing, pacing, and electrical response functions for correcting bradycardia and pathologic tachycardia.

26. The method of claim 24, including making available rate-adaptive pacing among said plurality of different pacing therapy modes, by use of an accelerometer for sensing physical activity of the patient to initiate the rate-adaptive pacing when the pacing mode therefor is selectively enabled for current operation.

27. The method of claim 24, wherein said pacemaker is further adapted for selectively performing additional memory and logic functions to store and analyze events pertaining to malfunction of the patient's cardiovascular system and to the operation of the pacemaker in response thereto, said method further comprising the steps of selectively enabling said additional memory and logic functions to programmably upgrade the pacemaker non-invasively when implanted in the patient, and subsequently retrieving the stored events by telemetry for physician diagnosis of the patient's condition from which to consider modification of the pacemaker functions.

28. The method of claim 24, wherein said pacemaker is further adapted to selectively perform a function of monitoring signals indicative of physiological parameters of the patient other than electrical activity of the heart, said method further comprising the steps of non-invasively programming the pacemaker to selectively enabling said function of physiological signal monitoring, and subsequently retrieving the monitored information by telemetry for physician diagnosis.

29. A programmable multi-mode cardiac pacemaker device adapted to be implanted in the body of a patient and upgraded from time to time to enable the device to provide appropriate treatment of arrhythmias attributable to abnormalities in the cardiac pacing or cardiovascular system of the patient, as the needs of the patient for such treatment undergo change, said device comprising means for providing a multiplicity of different pacing operating modes in which electrical stimuli are produced for selective application to the patient's heart to treat arrhythmias; means for selectively sensing electrical activity of the patient's heart; means for selectively enabling said mode providing means to operate in at least one of said modes selected to produce electrical phenomena designated to treat a diagnosed arrhythmia of the patient; means responsive to detecting the occurrence of the diagnosed arrhythmia from sensed atrial or ventricular electrical activity for producing the designated electrical phenomena: means for programming said device to non-invasively disable those of said multiplicity of pacing operating modes which are not required to produce the designated electrical phenomena; and means for selectively restoring disabled pacing operating modes. including means for precluding said selective restoration except upon access through a security code and further including means for providing a warning signal in response to all of said multiplicity of pacing operating modes having been disabled. —

30. A method for selectively non-invasively upgrading a programmable multi-mode cardiac pacemaker device adapted to be implanted in the body of a patient to enable the device to provide appropriate treatment of arrhythmias attributable to abnormalities in the cardiac pacing or cardiovascular system of the patient, as the needs of the patient for such treatment undergo change from time to time, said method comprising the steps of providing the device with a plurality of different programmable diagnostic, memory, and operating functional modes in which respective electrical pulse waveforms are produced for selective application to the patient's heart to treat arrhythmias; selectively sensing electrical activity of the patient's heart; programming the device to enable operation thereof in at least one of said modes selected to produce an electrical pulse waveform designated to treat an arrhythmia when diagnosed in the patient in response to detection of the occurrence of the diagnosed arrhythmia from sensed electrical activity of at least one of the atrial and ventricular chambers of the heart, while leaving those of said plurality of modes which are not required to produce the electrical pulse waveform designated to treat the diagnosed arrhythmia initially disabled; and selectively restoring one or more of said disabled modes when needed to upgrade the device, only upon access through a security code; and further including signaling an event in which none of said functional modes is enabled for operation after the device is implanted.

* * * * *